United States Patent [19]

Takano et al.

[11] Patent Number: 5,100,655
[45] Date of Patent: Mar. 31, 1992

[54] ARGININE DERIVATIVES AND COSMETIC COMPOSITIONS CONTAINING THE SAME

[75] Inventors: Shinichi Takano; Tohru Kobayashi; Takeshi Miyoshi; Masahiro Takehara, all of Kawasaki, Japan

[73] Assignee: Ajinomoto Co., Ltd., Tokyo, Japan

[21] Appl. No.: 647,206

[22] Filed: Jan. 28, 1991

Related U.S. Application Data

[63] Continuation of Ser. No. 286,294, Dec. 19, 1988, abandoned.

[30] Foreign Application Priority Data

Dec. 18, 1987 [JP] Japan .................... 62-320992
Sep. 16, 1988 [JP] Japan .................... 63-231666
Sep. 22, 1988 [JP] Japan .................... 63-238480
Nov. 10, 1988 [JP] Japan .................... 63-284700

[51] Int. Cl.$^5$ .............. A61K 7/475; C07C 229/00; B01F 00/00; C11D 3/26
[52] U.S. Cl. ...................... 424/63; 252/8.6; 252/546; 252/356; 252/357; 252/DIG. 13; 514/785; 514/788; 514/937; 514/938; 424/70; 560/168
[58] Field of Search ........... 260/404.5; 564/230; 252/357, 544, 546, DIG. 13, 356; 560/168; 514/788, 937, 938, 785; 424/70

[56] References Cited

U.S. PATENT DOCUMENTS 3,825,560 7/1974 Saito et al. .................. 560/168 X

FOREIGN PATENT DOCUMENTS 22055 7/1976 Japan .
181206 10/1984 Japan .
A1352420 5/1974 United Kingdom .

OTHER PUBLICATIONS

Patent Abstracts of Japan, vol. 1, No. 131 (2903) (C77), 28th Sep. 1977; & JP-A-52 83604 (Mitsubishi Kasei Kogyo) 7th Dec. 1977.
Chemical Abstracts, vol. 101, No. 2, 9th Jul. 1984, p. 289, Abstract No. 12017c, Columbus, Ohio, US; Lion Corp.: Hair Conditioners Containing . . .
Chemical Abstracts, vol. 85, No. 16, 18th Oct. 1976, p. 105, Abstract No. 110386t, Columbus, Ohio, US: Yoshida et al.: Surfactants derived from . . .

*Primary Examiner*—Thurman K. Page
*Assistant Examiner*—Susan S. Rucker
*Attorney, Agent, or Firm*—Oblon, Spivak, McClelland, Maier & Neustadt

[57] ABSTRACT

Emulsifier compositions capable of forming an emulsion which is stable over a wide range of temperatures and contains at least one of a N$^\alpha$-long-chain acyl arginine higher alkyl ester of the general formula (I) or an acid-addition salt thereof:

$$R^1CONHCHCOOR^2 \quad \underset{\underset{CH_2CH_2CH_2NHC-NH_2}{\|}}{NH} \quad (I)$$

wherein R$^1$CO is a straight-chain C$_{8-22}$ acyl group; and R$^2$ is a straight-chain or branched C$_{12-22}$ alkyl group, are disclosed.

12 Claims, No Drawings

ARGININE DERIVATIVES AND COSMETIC COMPOSITIONS CONTAINING THE SAME

This application is a continuation of application Ser. No. 286,294, filed on Dec. 19, 1988, now abandoned.

BACKGROUND OF THE INVENTION

1. Field of the Invention

This invention relates to cosmetics for the skin such as milky lotions and creams, medicines for external use such as ointments, cosmetics for the hair such as shampoos, rinses, hair treatment solutions and hair conditioners, softeners, etc.

2. Discussion of the Background

Emulsifier compositions which are obtained by the emulsification of oily and aqueous components (such as a milky lotion, cream, ointment, or hair treatment solutions) are prepared by employing an appropriate mixture of a hydrophilic emulsifier and a lipophilic emulsifier, which mixture depends on the hydrophiliclipophilic balance of the oily component. More particularly, a composition containing an anionic surface active agent and a nonionic surface active agent of the ether, ester or amide type is usually employed as an emulsifier for preparing an emulsion.

It has however been very difficult to maintain the emulsifying property of such emulsifier composition at a constant level at high and low temperatures and for long periods of time. A greater deal of effort has heretofore been required for selecting appropriate component from the wide variety of emulsifiers available and employing this component in an appropriate ratio when it is mixed with the other components.

There is therfore a need for an emulsifier having improved emulsifiability.

SUMMARY OF THE INVENTION

Accordingly, it is an object of this invention to provide novel arginine derivatives which can be used to provide emulsifier compositions which can form emulsions which are stable over a wide range of temperatures.

The present invention provides arginine derivatives of the formula (I):

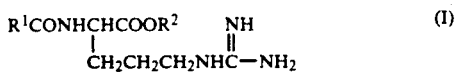

wherein
$R^1CO$ is a straight-chain $C_{8-22}$ acyl group; and
$R^2$ is a straight-chain or branched $C_{12-22}$ alkyl group; and
salts obtained by adding an acid to the compounds of formula (I).

The arginine derivatives of formula (I) can emulsify oily and aqueous components uniformly to form a stable emulsion. They can form an O/W (oil/water) or a W/O (water/oil) emulsion as desired if the proportions of the oily and aqueous components are appropriately varied or if another appropriate emulsifier is added.

The emulsifier compositions containing the arginine derivative of this invention can be used to provide, for example, cosmetics for the skin such as milky lotions and creams, medicines for external use such as ointments, cosmetics for the hair such as shampoos, rinses, hair treatment solutions and hair conditioners, and softeners.

DETAILED DESCRIPTION OF THE PREFERRED EMBODIMENTS

The present arginine derivatives are particularly useful when employed in cosmetics for hair or softeners, because the arginine derivatives are adsorbed by the hair, or by fibers such as wool or cotton fibers. In these uses, the present arginine derivatives have been found to exhibit, among others, the following advantages:

(1) they remove the roughness of the hair or fibers rendering them soft to the touch;

(2) they smoothen the hair or fibers rendering them easy to comb;

(3) they prevent the generation of static electricity in the hair or fabric;

(4) they give a pleasant and oily feel, such as a smooth or moist feel; and (5) they have a very low degree of irritability towards the skin of the head or to the eyes.

The inventors have found that an emulsifier composition can form an emulsion which is stable over a wide range of temperatures if it contains at least one of a $N^\alpha$-long-chain acyl arginine higher alkyl ester of the general formula (I) or an acid-addition salt thereof (hereinafter referred to as the arginine derivative):

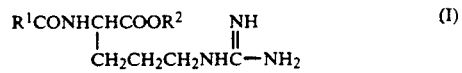

wherein
$R^1CO$ is a straight-chain $C_{8-22}$ acyl group; and
$R^2$ is a straight-chain or branched $C_{12-22}$ alkyl group.

The arginine derivatives according to this invention are novel compounds which can be manufactured easily and at a low cost using generally known methods. For example, these compounds can be obtained if (1) a halogenated $C_{8-22}$ acyl compound and arginine are condensed in the presence of a base and (2) the resulting $N^\alpha$-long-chain acyl arginine and a primary, secondary or tertiary $C_{12-22}$ alcohol are esterified in the presence of an acid catalyst. Examples of acid catalysts which can be employed include hydrogen halides such as hydrogen chloride or bromide, and Broensted acid such as sulfuric, nitric, phosphoric, trifluoroacetic or p-toluenesulfonic acid, a cation exchange resin and Lewis acids such as aluminum chloride The arginine derivative may be either an optically active substance or a racemic mixture. The salts of the arginine derivative which can be employed include inorganic acid salt such as hydrochloride, sulfate, hydrobromide, hydroiodide or phosphate, or organic acid salts such as acetate, citrate, p-toluenesulfonate, a fatty acid salt, succinate, maleate, lactate, tartrate, glutamate, aspartate or pyrrolidonecarboxylate.

Specific examples of the arginine derivative according to this invention include $N^\alpha$-cocoyl-L-arginine stearyl ester hydrochloride, $N^\alpha$-lauroyl-L-arginine stearyl ester lactate, $N^\alpha$-lauroyl-L-arginine palmityl ester succinate, $N^\alpha$-lauroyl-L-arginine stearyl ester citrate, $N^\alpha$-myristoyl-DL-arginine stearyl ester sulfate, $N^\alpha$-palmitoyl-L-arginine lauryl ester hydrochloride, $N^\alpha$-palmitoyl-DL-arginine palmityl ester malate, $N^\alpha$-stearoyl-L-arginine stearyl ester phosphate, $N^\alpha$-stearoyl-L-arginine stearyl ester DL-pyrrolidonecarboxylate, hardened beef tallow fatty acid acyl-L-arginine lauryl ester hydrochloride, N$^\alpha$-cocoyl-L-arginine palmityl ester glutamate, N$^\alpha$-L-arginine laurylester aspartate, N$^\alpha$-octanoyl-L-arginine-myristyl ester hydrochloride, N$^\alpha$-cocoyl-L-arginine isostearyl ester hydrochloride, and N$^\alpha$-myristoyl-L-arginine octyldodecyl ester hydrochloride.

The emulsifier composition of this invention can emulsify oily and aqueous components uniformly to form a stable emulsion over a wide range of temperatures.

Examples of the oily components which can be employed to form an emulsion include hydrocarbons such as liquid paraffin, squalane, vaseline and microcrystalline wax; oils and fats such as olive oil, coconut oil, tsubaki oil, Japan wax and castor oil; waxes such as beeswax, spermaceti, jojoba oil, lanolin and carnauba wax; higher fatty acids such as lauric acid, myristic acid, palmitic acid, stearic acid, isostearic acid, oleic acid and lanolin fatty acid; higher alcohols such as lauryl alcohol, myristyl alcohol, cetanol, stearyl alcohol, cetostearyl alcohol, oleyl alcohol, cholesterol, lanolin alcohol and octyl dodecanol; and esters such as cetyl lactate, tri(capryl caprylic acid) glyceryl ester, hexyl laurate, glycerol trilaurate, isopropyl myristate, octyldodecyl myristate, cetyl myristate, myristyl myristate, glycerol trimyristate, isopropyl palmitate, butyl stearate, octyldodecyl oleate, decyl oleate, N-acyl glutamic acid higher alcohol diester, N-acyl glutamic acid polyoxyethylene octyldodecyl ether diester and hardened oil.

Examples of the aqueous components which can be employed include purified water, glycerol, propylene glycol, 1,3-butylene glycol, sorbitol, polyethylene glycol, hexylene glycol, hydrolytic protein, amino acid, sodium pyrrolidonecarboxylate and sodium lactate; humidifying agents such as sodium hyaluronate, water-soluble chitin, chitosan and derivatives thereof; alcohols such as ethyl alcohol and isopropanol; and salts.

Salts have hitherto been difficult to employ because they have an adverse effect on the nonionic surface active agent which have heretofore usually been employed as emulsifiers. It is however possible to use salts with the arginine derivative of this invention, as the emulsifying properties of the present arginine derivatives are hardly influenced by any such salt.

A thickener can also be added to the emulsifier composition of this invention to control its viscosity. Examples of thickeners which can be employed include high molecular thickeners such as carboxyvinyl polymer, sodium polyacrylate, sodium alginate, propylene glycol alginate, sodium carboxymethyl cellulose, methyl cellulose, ethyl cellulose, hydroxyethyl cellulose, hydroxypropyl cellulose, polyethylene glycol distearate and polyoxyethylene (120)-methyl glucose dioleate; and colloidal hydrated silicates such as colloidal hydrated aluminum silicate (bentonite) and colloidal hydrated aluminum magnesium silicate.

Although the emulsifier composition consisting solely of the arginine derivative according to formula (I) can form a stable emulsion, it can also contain an emulsifier which is conventionally employed, depending on the purpose for which composition is used.

Examples of the conventional emulsifier which can be employed include anionic surface active agents such as polyoxyethylene alkyl ether, polyoxyethylene cholesteryl ether, polyoxyethylene sorbitan fatty acid partial ester, polyoxyethylene sorbitol fatty acid partial ester, polyoxyethylene glycerol fatty acid partial ester, polyoxyethylene phosphoric acid ester, polyoxyethylene fatty acid monoester, polyoxyethylene hardened castor oil, polyoxyethylene hardened castor oil fatty acid ester, polyglycerol fatty acid ester, cane sugar fatty acid ester, N-acyl glutamic acid polyoxyethylene alkyl ether diester, monopyroglutamic acid monofatty acid polyoxyethylene hardened castor oil, monopyroglutamic acid monofatty acid polyoxyethylene glycerol, monopyroglutamic acid monofatty acid glycerol, monofatty acid ethylene glycol, monofatty acid propylene glycol, sorbitan fatty acid partial ester, glycerol fatty acid partial ester, fatty acid alkanol amide, alkylamine oxide, N-acyl glutamic acid, N-acyl aspartic acid, and other N-acyl acidic amino acids, or salts thereof; and cationic surface active agents such as lower alkyl esters of N-long-chain acyl basic amino acids. Each of the alkyl group, acyl group (residual group of fatty acid), etc. noted above may have 8 to 22 carbon atoms.

The emulsifier composition of this invention can form an O/W or W/O emulsion if the proportions of its oily and aqueous components are appropriately varied, or if another appropriate emulsifier is added thereto.

Although the amount of the arginine derivative which the emulsifier composition of this invention can contain may depend on the purpose for which it is used, this amount usually ranges from 0.1 to 10% by weight.

The emulsifier composition of this invention may further contain a preservative, an ultraviolet absorbing agent, a pigment, a perfume, an extract of a crude drug, or other additives, if such additives are required for attaining the purpose for which the composition is used.

The composition can be used for making, for example, cosmetics for the skin such as milky lotions and creams, medicines for external use such as ointments, cosmetics for the hair such as shampoos, rinses, hair treatment solutions and hair conditioners, and softeners. It is particularly useful when used for making a cosmetic for the hair and a softener, as the arginine derivative is adsorbed by the hair and fibers, such as of wool or cotton, and renders them very soft, antistatic and smooth.

Quaternary ammonium sals have usually been employed for imparting softness, antistatic property and smoothness to the hair, or fibers such as of wool and cotton, but there is concern about the safety of their use. On the other hand, the present arginine derivatives are very safe and are, therefore, suitable for any cosmetic for the hair, or softener.

When the composition of this invention is employed for making a cosmetic for the hair or a softener, it may contain other components in addition to the arginine derivative of formula (I), the oily and aqueous components and the thickener if it does not depart from the spirit of this invention. More specifically, it may contain an anionic surface active agent.

Examples of anionic surface active agents which can be employed include N-acyl acidic amino acids or salts thereof, such as long-chain fatty acid salt, alkyl sulfate, polyoxyethylene alkyl ether sulfate, alkyl sulfonate (SAS), $\alpha$-olefin sulfonate (AOS), monoalkyl sulfosuccinate, dialkyl sulfosuccinate, polyoxyethylene alkyl sulfosuccinate, acyl monoethanolamide polyoxyethylene sulfosuccinic acid monoester, monoalkyl phosphate, polyoxyethylene alkyl ether phosphate, acyl methyl taurine salt, acyl isethionate, N-acyl glutamic acid and N-acyl aspartic acid; and N-acyl neutral amino acids or salts thereof, such as N-acyl proline, N-acyl serine, Nacyl sarcosine and N-acyl methyl $\beta$-alanine. The anionic surface active agent which can be employed is one in which the alkyl and acyl groups have 8 to 22 carbon atoms.

If any salt is employed, it is preferable to use a lithium, potassium, sodium or triethanolamine salt, or a basic amino acid salt, such as of lysine or arginine.

Examples of the cationic surface active agent which can also be used with arginine derivative of this invention include alkyltrimethyl ammonium salts, dialkyldimethyl ammonium salts, alkyldimethylbenzyl ammonium salts, alkyl pyridinium salts, dipolyoxyethylene alkylmethyl ammonium salts, tri(polyoxyethylene)alkyl ammonium salts, and 2-alkyl-1-alkyl-1-hydroxyethyl imidazolinium salts. The cationic surface active agent which can be employed is one in which the alkyl group has 8 to 22, preferably 16 to 22, carbon atoms. Alkyl groups having 16 to 22 carbon atoms are preferred from the standpoint of safety.

The type of salts which can be employed are salts in which the counter ions are a halogen atom, such as chlorine or bromine. Other examples of cationic surface active agent which can be employed include lower alkyl esters of N-long-chain acyl basic amino acids, such as N-cocoyl-L-arginine ethyl ester . DL-pyrrolidone carboxylate.

Examples of the amphoteric surface active agent which can be employed include alkyldimethyl aminoacetic acid betaine, 2-alkyl-N-carboxymethyl-Nhydroxyethyl imidazolinium betaine, higher fatty acid amide propyldimethyl aminoacetic acid betaine, N-alkyl-N,Ndimethyl-N-sulfoalkylene ammonium betaine, and N-mono long-chain acyl-N,N-dimethyl lysine. The alkyl group and the acyl group (residual group of fatty acid) of these materials are each required to have 8 to 22 carbon atoms.

The composition may further contain polyvinyl alcohol, polyvinyl acetate, tragacanth gum, shellac, a methoxyethylene-maleic anhydride copolymer, polyvinyl pyrrolidone, a polyvinyl pyrrolidone-vinyl acetate copolymer, a polyvinyl pyrrolidone-dimethylaminoethyl methacrylic acid copolymer, polypeptide, cationized cellulose, lecithin, methyl polysiloxane, methylphenyl polysiloxane, cyclic and other silicones, polyoxypropylene butyl ether, or any other film-forming agent; and N-lauroyl-L-lysine, zinc pyrithione, 1-hydroxy-2-pyridone salt, or any other agent for removing and/or controlling dandruff.

The emulsifier composition of this invention can be manufactured as easily as any conventional cleansing agent. It can, for example, be manufactured if the oily and aqueous components are mixed separately with heating, then mixed together, and the mixture subsequently cooled to room temperature. It can be manufactured easily by employing any conventional apparatus.

Having generally described this invention, a further understanding can be obtained by reference to certain specific examples which are provided herein for purposes of illustration only and are not intended to be limiting unless otherwise specified.

EXAMPLE 1

Synthesis of $N^\alpha$-lauroyl-L-argininestearyl ester hydrochloric salt (A):

Twenty grams of $N^\alpha$-lauroyl-L-arginine, 16.7 g of stearyl alcohol and 20.0 g of 3A molecular sieves were added to 400 ml of toluene. The mixture was stirred in an ice bath, and then hydrochloride gas was bubbled into the mixture, which was then allowed to stand overnight at room temperature. The 3A molecular sieves were separated by filtration and then the concentrated filtrate was redissolved with 800 ml of acetone, and then cooled and filtered. The residue was washed with acetone and dried under reduced pressure to obtain 30.5 g of white crystals (A) (84.2%). The physical data of m.p. MS, IR of compound (A) are shown in table 1.

EXAMPLE 2

$N^\alpha$-Lauroyl-L-argininepalmityl ester hydrochloric acid salt (B) was obtained by following the procedure outlined in example 1 using palmityl alcohol (14.9 g) instead of stearylalcohol. The yield was 27.0 g (78.0%). The physical data of compound (B) are shown in table 1.

EXAMPLE 3

$N^\alpha$-Lauroyl-L-argininelauroyl ester hydrochloric acid salt (C) was synthesized by following the procedure outlined in example 1 using lauroyl alcohol (11.5 g) instead of stearyl alcohol. The yield was 21.3 g (67.6%). The physical data of compound (C) are shown in table 1.

EXAMPLE 4

$N^\alpha$-palmitoyl-L-argininelauryl ester hydrochloric acid salt (D) was obtained by following the procedure outlined in example 1 using $N^\alpha$-palmitoyl-L-arginine (20.0 g) and laurylalcohol (9.9 g) instead of $N^\alpha$-lauroyl-L-arginine and stearylalcohol. The yield was 23.1 g (77.3%) The physical data of compound (D) are shown in table 1.

EXAMPLE 5

$N^\alpha$-palmitoyl-L-argininepalmityl ester hydrochloric acid salt (E) was synthesized by following the procedure outlined in example 1 using $N^\alpha$-palmitoyl-L-arginine (20.0 g) and palmityl alcohol (12.9 g) instead of $N^\alpha$-lauroyl-L-arginine and stearylalcohol. The yield was 26.5 g (81.3%). The physical data of compound (E) are shown in table 1.

EXAMPLE 6

$N^\alpha$-palmitoyl-L-argininestearyl ester hydrochloric acid salt (F) was obtained by following the procedure outlined in example 1 using $N^\alpha$-palmitoyl-L-arginine (20.0 g) and stearyl alcohol (14.4 g) instead of $N^\alpha$-lauroyl-L-arginine. The yield was 29.0 g (85.3%).

The physical data of compound (F) are shown in table 1.

EXAMPLE 7

$N^\alpha$-stearoyl-L-argininelauryl ester hydrochloric acid salt (G) was synthesized by following the procedure outlined in example 1 using $N^\alpha$-stearoyl-L-arginine (20.0 g) and laurylalcohol (8.6 g) instead of $N^\alpha$-lauroyl-L-arginine and stearylalcohol. The yield was 24.3 g (83.2%). The physical data of compound (G) are shown in table 1.

EXAMPLE 8

$N^\alpha$-stearoyl-L-argininepalmityl ester hydrochloric acid salt (H) was obtained by following the procedure outlined in example 1 using $N^\alpha$-stearoyl-L-arginine (20.0 g) and palmitylalcohol (11.1 g) instead by $N^\alpha$-lauroyl-L-arginine and stearyl alcohol. The yield was 25.5 g (80.2%). The physical data of compound (H) are shown in table 1.

EXAMPLE 9

$N^\alpha$-stearoyl-L-argininestearyl ester hydrochloric acid salt (I) was obtained by following the procedure outlined in example 1 using $N^\alpha$-stearoyl-L-arginine (20.0 g) and stearyl alcohol (12.3 g) instead of $N^\alpha$-lauroyl-L-arginine. The yield was 28.2 g (85.2%). The physical data of compound [I] are shown in table 1.

EXAMPLE 10

$N^\alpha$-cocoyl-L-arginine stearyl ester hydrochloric acid salt (J) was obtained by following the procedure outlined in example 1 using $N^\alpha$-cocoyl-L-arginine (70.2 g) and stearyl alcohol (52.1 g) instead of $N^\alpha$-lauroyl-L-arginine. The yield was 104.5 g (83.0%). The physical data of compound (J) are shown in table 1.

TABLE 1

| Example | Compound | Physical data of the novel arginine derivatives | | |
|---|---|---|---|---|
| | | m.p. (°C.) | MS (m/e) | IR (cm$^{-1}$) |
| 1 | $N^\alpha$-Lauroyl-L-arginine-stearyl ester hydrochloric acid salt | 93.3 | 609 | 1740 |
| 2 | $N^\alpha$-Lauroyl-L-arginine-palmityl ester hydrochloric acid salt | 88.6 | 581 | 1740 |
| 3 | $N^\alpha$-Lauroyl-L-arginine-lauryl ester hydrochloric acid salt | 94.5 | 525 | 1740 |
| 4 | $N^\alpha$-Palmitoyl-L-arginine-lauryl ester hydrochloric acid salt | 93.0 | 581 | 1730 |
| 5 | $N^\alpha$-Palmitoyl-L-arginine palmityl ester hydrochloric acid salt | 84.2 | 637 | 1730 |
| 6 | $N^\alpha$-Palmitoyl-L-arginine-stearyl ester hydrochloric acid salt | 80.9 | 665 | 1730 |
| 7 | $N^\alpha$-Stearoyl-L-arginine-lauryl ester hydrochloric acid salt | 89.4 | 609 | 1740 |
| 8 | $N^\alpha$-Stearoyl-L-arginine-palmitoyl ester hydrochloric acid salt | 76.8 | 665 | 1740 |
| 9 | $N^\alpha$-Stearoyl-L-arginine-stearyl ester hydrochloric acid salt | 76.5 | 693 | 1740 |
| 10 | $N^\alpha$-Cocoyl-L-arginine-stearyl ester hydrochloric acid salt | 114.2 | 581 609 637 665 | 1740 |

EXAMPLES 11-15 AND COMPARATIVE EXAMPLE 1

The emulsifier compositions shown in table 2 were prepared and allowed to stand for a month at 45° C. and −5° C. and a microscopic observation (×400) of the stability of emulsion was made. The results shown in the table 2 showed that the emulsified compositions of this invention were more stable than the comparative composition (comparative example 1) which used a conventional emulsifier, at both 45° C. and −5° C.

In table 2, 0 = uniform emulsion, Δ = partial aggregation, and x = aggregation.

TABLE 2

| | wt. % | | | | | |
|---|---|---|---|---|---|---|
| | Example | | | | | Comparative |
| | 11 | 12 | 13 | 14 | 15 | Example 1 |
| $N^\alpha$-Cocoylarginine-stearyl ester | 3.0 | | | 2.5 | 2.0 | |
| $N^\alpha$-Stearoylarginine palmityl ester hydrochloric acid salt | | 3.0 | | | | |
| $N^\alpha$-Lauroylarginine-palmityl ester acetic acid salt | | | 3.0 | | | |
| P.O.E. (20) sorbitane monostearate | | | | 0.5 | | 2.0 |
| Sorbitane monostearate | | | | | 1.0 | 1.0 |
| Liquid paraffin | 27.0 | 27.0 | 27.0 | 27.0 | 27.0 | 27.0 |
| Cetanol | 3.0 | 3.0 | 3.0 | 3.0 | 3.0 | 3.0 |
| Stearyl aclohol | 3.0 | 3.0 | 3.0 | 3.0 | 3.0 | 3.0 |
| Propylene glycol | 5.0 | 5.0 | 5.0 | 5.0 | 5.0 | 5.0 |
| Water | bal. | bal. | bal. | bal. | bal. | bal. |
| Stability of emulsion: | | | | | | |
| 45° C. | 0 | 0 | 0 | 0 | 0 | Δ |
| room temperature | 0 | 0 | 0 | 0 | 0 | 0 |
| −5° C. | 0 | 0 | 0 | 0 | 0 | X |

EXAMPLES 16-18 AND COMPARATIVE EXAMPLES 2-4

Hair washed with an emulsifier (Emarl 20C made by Kao Chemicals) was preserved in 0.1% arginine derivatives aqueous solution for one minute, to observe the antistatic effect of the arginine derivatives of this invention obtained by example 1-3.

The treated hair was washed with water and dried. The antistatic value was measured and are reported in table 3. The results showed the antistatic value of the hair treated with the arginine derivatives is smaller than that treated with the conventional emulsifier (comparative example 2: trimethylstearylammonium chloride, and comparative example 3: $N^\alpha$-cocoyl-L-arginineethyl ester.DL-pyrrolidone carboxylic acid salt), and with a nontreated hair (comparative example 4). These results show that the arginine derivatives of this invention have a good antistatic effect.

The coefficient friction of the hair treated with an arginine derivatives aqueous solution were measured and are reported in table 3. The results show that the coefficient of friction of hair treated in accordance with this invention was smaller than that of hair treated with conventional cation surfactants (comparative example 2: trimethylstearylammonium chloride, and comparative example 3: $N^\alpha$-cocoyl-L-arginineethyl ester.DL-pyrrolidone carboxylic acid salt), and with the nontreated hair. These results show that the arginine derivatives of this invention have good smoothness. The hair treated with the arginine derivatives was hair free of oil and which could easily be combed.

TABLE 3

| Example | Compound | Antistatic value × 10$^{-8}$Q | Coefficient friction |
|---|---|---|---|
| 16 | $N^\alpha$-Lauroyl-L-argininestearyl ester hydrochloric acid salt | 0.13 | 0.14 |
| 17 | $N^\alpha$-Lauroyl-L-argininepalmityl | 0.14 | 0.15 |

TABLE 3-continued

|  | Compound | Antistatic value × $10^{-8}Q$ | Coefficient friction |
|---|---|---|---|
|  | ester hydrochloric acid salt |  |  |
| 18 | $N^\alpha$-Lauroyl-L-argininelauryl ester hydrochloric acid salt | 0.14 | 0.16 |
| Comparative example |  |  |  |
| 2 | Trimethylstearyl-ammonium chloride | 0.16 | 0.17 |
| 3 | $N^\alpha$-cocoyl-L-arginineethyl ester hydrochloric acid salt | 0.16 | 0.17 |
| 4 | untreated | 0.67 | 0.28 |

(cf 1) The antistatic value was measured by Universal-Electrometer (MMAI-17) (made by KAWAGUCHI INDUSTRY Co. Ltd.)
(cf 2) A Coefficient friction was measured by the Friction Tester (KES-SE) (made by KATOHTECH Co. Ltd.)

EXAMPLE 19

Milky Lotion

A lotion of the composition shown in table 4 was prepared to obtain a stable emulsion.

TABLE 4

| Composition | wt. % |
|---|---|
| $N^\alpha$-Cocoyl-L-argininestearyl ester hydrochloric acid salt | 3.0 |
| Stearic acid | 0.2 |
| Cetanol | 1.5 |
| Vaseline oil | 3.0 |
| Lanolin alcohol | 2.0 |
| Liquid paraffin | 10.0 |
| Glycerine | 3.0 |
| Propylene glycol | 5.0 |
| Triethanol amine | 1.0 |
| Perfume | 0.5 |
| Antiseptic | 0.3 |
| Water | balance |

EXAMPLE 20

Emollient Cream

The following components were compounded to prepare an emollient cream. The stability of the emulsion was good.

TABLE 5

| Composition | wt. % |
|---|---|
| $N^\alpha$-Lauroyl-L-arginineisostearyl ester lactic acid salt | 3.0 |
| Bees was | 6.0 |
| Cetanol | 5.0 |
| Reduced Lanolin | 8.0 |
| Squalene | 37.0 |
| Monoglyceride | 4.0 |
| Sorbitan monostearate | 1.0 |
| Chitin (partially deactificated 40-60%) | 0.4 |
| Propylene glycol | 5.0 |
| Perfume | 0.2 |
| Water | balance |

EXAMPLE 21

Cold Cream

The materials shown in table 6 were compounded in the amounts shown to prepare a cold cream.

TABLE 6

| Composition | wt. % |
|---|---|
| $N^\alpha$-Lauroyl-DL-arginine myristyl ester sulfuric acid salt | 2.0 |
| Liquid paraffin | 20.0 |
| Solid paraffin (m.p. 42-44° C.) | 9.0 |
| Isopropyl palmitate | 3.0 |
| Cetanol | 1.0 |
| Lanolin | 2.0 |
| Nikkol WCB | 10.0 |
| Sorbitan monostearate | 1.5 |
| Polyoxyethylene sorbitan monooleate (20) | 1.5 |
| Sodium pyroglutamate (50%) | 3.0 |
| Antiseptic | 0.2 |
| Perfume | 0.2 |
| Water | balance |

EXAMPLE 22

Hair Rinse Treatment Composition

The composition shown in table 7 was prepared to obtain a hair rinse treatment composition.

TABLE 7

| Composition | wt. % |
|---|---|
| $N^\alpha$-Stearoyl-DL-arginine lauryl ester DL-pyrrolidone carboxylic acid | 2.0 |
| Diglyceride | 2.0 |
| Liquid paraffin | 3.0 |
| Stearic acid | 1.5 |
| Polyoxyethylene (5) stearyl ether | 1.0 |
| Propylene glycol | 10.0 |
| Perfume | 0.5 |
| Water | balance |

EXAMPLE 23

Ointment (O/W Type)

The following components were compounded to prepare a O/W type ointment.

TABLE 8

| Composition | wt. % |
|---|---|
| $N^\alpha$-Cocoyl-L-argininestearyl ester hydrochloric acid salt | 2.0 |
| White vaseline | 25.0 |
| Stearyl alcohol | 22.0 |
| Propylene glycol | 12.0 |
| Sodium laurylsulfurate | 15.0 |
| Ethyl paraoxybenzoate | 0.3 |
| Propyl paraoxybenzoate | 0.1 |
| Perfume | 0.2 |
| Water | balance |

EXAMPLE 24

Hair Rinse Composition

The materials shown in table 9 were compounded in the amounts shown to prepare a hair rinse composition.

TABLE 9

| Composition | wt. % |
|---|---|
| $N^\alpha$-Cocoyl-L-argininestearyl ester hydrochloric acid salt | 1.0 |
| Sodium $N^\alpha$-lauroylsalcosine | 0.3 |
| Polymer JR-400 (Union Carbide) | 0.3 |
| Cetyl alcohol | 1.0 |
| Stearyl alcohol | 1.0 |
| Propylene glycol | 1.0 |
| Amiter LGOD-2.5 | 0.5 |
| Glycerine | 1.0 |
| Perfume | proper amount |

EXAMPLE 25

Hair Treatment Composition

A hair treatment composition was prepared according to the following formulation.

TABLE 10

| Composition | wt % |
|---|---|
| $N^\alpha$-Lauroyl-L-argininestearyl ester hydrochloric acid salt | 1.0 |
| 1-Hydroxy-2-pyrydon salt[1] | 0.5 |
| Liquid paraffin | 15.0 |
| Silicone[2] | 0.5 |
| Trimethyl stearyl ammonium chloride | 1.0 |
| Cetyl alcohol | 1.0 |
| Stearyl alcohol | 2.0 |
| Stearic acid | 0.5 |
| Glycerine monostearate | 1.0 |
| P.O.E. stearyl ether | 1.0 |
| Propylene glycol | 5.0 |
| Water | balance |

[1]
$$\text{CH}_3\text{—C(CH}_3)_2\text{—CH}_2\text{—CH}_2\text{—}\underset{\underset{O^-}{|}}{\underset{|}{N}}\overset{O}{\diagdown}\quad Na^+$$

[2]
$$\text{CH}_3\text{—Si(CH}_3)_2\text{—O—(Si(CH}_3)_2\text{—O)}_n\text{—Si(CH}_3)_2\text{—CH}_3$$

n = 10–50

EXAMPLE 26

Hair Condition

The following components were compounded to prepare a hair conditioner.

TABLE 11

| Composition | wt % |
|---|---|
| $N^\alpha$-Cocoyl-L-arginine stearyl ester DL-pyrrolidone carboxylic acid salt | 1.5 |
| Cocamide DEA (KAWAKEN Chemicals) | 1.5 |
| Liquid paraffine | 10.0 |
| Cetanol | 2.0 |
| Stearyl alcohol | 2.0 |
| Propylene glycol | 10.0 |
| Sorbitane monopalmitate | 1.0 |
| Tetraglycerin monostearate | 1.0 |
| Pyroter CPI-40 (AJINOMOTO CO., INC.) | 0.5 |
| Methyl parahydroxybenzoate | 0.1 |
| Collagen | 0.5 |
| Zinc pyrithion | 0.5 |
| Water | balance |

Hair treated with the hair conditioner had the characteristics of softness, smooth and good combability.

EXAMPLE 27 Hair Lotion

The following components were compounded to prepare a hair lotion.

TABLE 12

| Composition | wt % |
|---|---|
| $N^\alpha$-Cocoyl-L-arginine palmityl ester sulfuric acid salt | 1.0 |
| N-Stearoyl-L-Lysine propyl ester hydrochloric acid salt | 1.0 |
| Sodium hyaluronate | 0.5 |
| Cetanol | 1.0 |
| P.O.E. (5) sodium laurylethoxy sulfate | 1.0 |
| Propylene glycol | 4.0 |
| Ethanol | 2.0 |
| Squalan | 1.0 |
| Water | balance |

The hair treated with the hair lotion had the characteristics of smoothness, good combability and good arrangement.

EXAMPLE 28 Hair Rinse

TABLE 13

| Composition | wt % |
|---|---|
| $N^\alpha$-Cocoyl-L-arginine stearyl ester hydrochloric acid salt | 1.0 |
| Alkyl phosphate *1 | 4.0 |
| Chitin (partialy deacetificated 40–60%) | 0.1 |
| Cetanol | 5.0 |
| Liquid paraffine | 1.0 |
| P.O.E. stearyl ether | 1.5 |
| Propylene glycol | 5.0 |
| Isopropyl vinyl polymer | 0.5 |
| N-Lauroyl-L-Lysine | 0.5 |
| Water | balance |

*1 the mixture A and B. A/B = 1/9–9/1, n = 10–30

A: $[CH_3CH_2O(CH_2CHO)_n]_2\underset{\underset{O}{\|}}{\underset{|}{POH}}$
         $CH_3$ B: $CH_3CH_2O(CH_2CHO)_n\underset{\underset{O}{\|}}{\underset{|}{P(OH)_2}}$
          $CH_3$ Hair treated with the hair rinse had the characteristics of softness, smoothness and good combability.

EXAMPLE 29

Hair Brushing

The materials shown below were compounded in the amounts shown to prepare a hair brushing composition.

TABLE 14

| Composition | wt % |
|---|---|
| $N^\alpha$-Cocoyl-L-arginine stearyl ester hydrochloric acid salt | 0.5 |
| N-Lauroyl glutamic acid | 0.2 |
| Dimethyl silicone | 0.3 |
| Squalane | 0.2 |
| Propylene glycol | 0.2 |
| Perfume | 0.2 |
| Water | balance |

Hair treated with the hair brushing composition exhibited was softness, good combability and good arrangement.

EXAMPLE 30 Hair Rinse Composition

The following components were compounded to prepare a hair rinse composition.

TABLE 15

| Composition | wt % |
|---|---|
| $N^\alpha$-Palumitoyl-L-arginine lauryl ester hydrochloric acid salt | 1.5 |
| Stearyl alcohol | 2.0 |
| Propylene glycol | 6.0 |
| Perfume | 0.2 |

TABLE 15-continued

| Composition | wt. % |
| --- | --- |
| Water | balance |

Hair treated with the hair rinse had the characteristics of smoothness, softness, good combability and good arrangement.

EXAMPLE 31

Hair Shampoo

TABLE 16

| Composition | wt. % |
| --- | --- |
| $N^\alpha$-Lauroyl-L-arginine stearyl ester hydrochloric acid salt | 0.5 |
| Amisoft CS-11 (AJINOMOTO CO., INC.) | 5.0 |
| Amisoft CT-12 (30%) (AJINOMOTO CO., INC.) | 20.0 |
| Sodium lauryl ether sulfate (25%) | 20.0 |
| Cocamide CDE (KAWAKEN Chemicals) | 3.0 |
| Chitin (partially deacetificated) | 0.1 |
| Sodium chloride | 3.0 |
| P.O.E. (10) stearate | 1.0 |
| Cetanol | 1.0 |
| Glycerin monostearate | 2.0 |
| Perfume | 0.2 |
| Water | balance |

Hair treated with the hair shampoo was soft, had good combability and was smooth.

EXAMPLE 32

Hair Shampoo

The materials shown below were compounded in the shown amounts to prepare a hair shampoo.

TABLE 17

| Composition | wt. % |
| --- | --- |
| $N^\alpha$-Cocoyl-L-arginine stearyl ester sulfuric acid salt | 0.5 |
| Amisoft CT-12 (30%) (AJINOMOTO CO., INC.) | 45.0 |
| Cocamide CDE (KAWAKEN Chemicals) | 5.0 |
| Sodium DL-pyrrolydone carboxylate (50%) | 6.0 |
| P.O.E. (50%) Distearate | 3.0 |
| Ethylene glycol distearate | 1.5 |
| Behenyl alcohol | 1.0 |
| Perfume | 0.2 |
| Water | balance |

Hair treated with the hair shampoo has the characteristics of good cleaning, softness and smooth.

EXAMPLE 33

Softening Agent Composition

The following components were compounded to prepare a softening agent composition.

TABLE 18

| Composition | wt. % |
| --- | --- |
| $N^\alpha$-Cocoyl-L-arginine stearyl ester hydrochloric acid salt | 3.0 |
| Liquid paraffine | 2.0 |
| Cetyl alcohol | 1.0 |
| Propylene glycol | 2.0 |
| DL-pyrrolidone carboxylate | 0.5 |
| Perfume | 0.2 |
| Water | balance |

A cotton towel treated with the softening agent was soft and antistatic.

EXAMPLE 34

Softening Agent Composition

The following components were compounded in the shown amounts to prepare a softening composition.

TABLE 19

| Composition | wt % |
| --- | --- |
| $N^\alpha$-Lauroyl-L-arginine isostearyl ester lactic acid salt | 2.0 |
| Squalane | 2.0 |
| P.O.E. stearyl ether | 1.0 |
| Silicone *1 | 0.3 |
| Cetanol | 1.0 |
| Stearyl alcohol | 1.0 |
| Stearic acid | 0.5 |
| Glyceline monostearate | 1.0 |
| Propylene glycol | 1.0 |
| Water | balance |

*1
$$CH_3Si-O-\underset{\underset{CH_3}{|}}{\overset{\overset{CH_3}{|}}{Si}}-O-SiCH_3$$

$$(CH_3)_3Si-O(-Si(CH_3)_2-O)_n-Si(CH_3)_3 \quad n = 10-50$$

A cotton towel treated with the softening agent was soft and antistatic.

EXAMPLE 35

Softening Agent Composition

The following components were compounded to prepare a softening agent composition.

TABLE 20

| Composition | wt. % |
| --- | --- |
| $N^\alpha$-Stearoyl-D-arginine lauryl ester DL-pyrrolydone carboxylic acid salt | 2.5 |
| Cocamide propyl betaine CL (KAWAKEN Chemicals) | 1.5 |
| Liquid paraffine | 2.0 |
| Cetanol | 2.0 |
| Stearyl alcohol | 2.0 |
| Stearic acid | 1.0 |
| Plopylene glycol | 2.0 |
| Sorbitane monopalumitate | 0.5 |
| Tetraglycerine monostearate | 0.5 |
| Pyroter CPI-40 (AJINOMOTO CO., INC.) | 0.5 |
| Methyl parahydroxybenzoate | 0.1 |
| Water | balance |

A cotton towel treated with the softening agent was soft and antistatic.

EXAMPLE 36 Softening Agent Composition

A softening agent composition was prepared by using the compound outlined in table 21 in the amounts shown.

TABLE 21

| Composition | wt. % |
| --- | --- |
| $N^\alpha$-Cocoyl-L-arginine stearyl ester hydrochloric acid salt | 2.5 |
| N-Lauroyl glutamic acid | 0.5 |
| Squalane | 1.0 |
| Propylene glycol | 2.0 |
| Perfume | 0.2 |
| Water | balance |

A test piece made of wool was treated with the softening agent composition, and then evaluated. It was soft and antistatic.

EXAMPLE 37

The following components were compounded in the amounts shown to prepare a softening agent composition.

TABLE 22

| Composition | wt. % |
| --- | --- |
| $N^\alpha$-palmitoyl-L-arginine palmityl ester acetic acid salt | 4.0 |
| Trimethylstearyl ammonium chloride | 0.5 |
| Cetanol | 1.0 |
| P.E.O. (5) sodium lauroyl ethoxy sulfate | 1.0 |
| Carboxy vinyl chloride resin | 0.5 |
| Propylene glycol | 4.0 |
| Ethanol | 2.0 |
| Squalene | 1.0 |
| Water | balance |

A test piece of wool treated with the softening agent composition was soft, smooth, antistatic and emollient.

EXAMPLE 38 Emollient Lotion

The materials shown in table 23 were compounded in the amounts shown to prepare an emollient lotion.

TABLE 23

| Composition | wt. % |
| --- | --- |
| $N^\alpha$-Lauroyl-L-argininestearyl ester acetic acid salt | 8.0 |
| Liquid paraffin | 22.0 |
| α-Octyl dodecyl mylistate | 1.5 |
| Amiter LGOD-2 (AJINOMOTO CO., INC.) | 0.5 |
| Pyroter GPI-25 (AJINOMOTO CO., INC.) | 0.5 |
| Cetanol | 1.1 |
| Polyethylene glycol 1000 | 0.2 |
| Amisoft LS-11 (AJINOMOTO CO., INC.) | 0.1 |
| Propylene glycol | 5.0 |
| Glycerine | 3.0 |
| Methyl parahydroxybenzoate | 0.1 |
| Perfume | 0.3 |
| Water | balance |

The emulsion of the emollient lotion was stable for at least six months.

EXAMPLE 39 Vanishing Cream

The composition shown in table 24 was prepared to obtain a vanishing cream.

TABLE 24

| Composition | wt. % |
| --- | --- |
| $N^\alpha$-Cocoyl-L-argininestearyl ester hydrochloric acid salt | 0.5 |
| Stearic acid | 17.0 |
| Stearyl alcohol | 4.0 |
| Butyl stearate | 8.0 |
| Glycerine monostearyl ester | 1.5 |
| Propylene glycol | 10.0 |
| Glycerin | 4.0 |
| Perfume | 0.2 |
| Water | balance |

The emulsion of the vanishing cream was very stable for at least six months.

What is claimed as new and desired to be secured by Letters Patent of the United States is:

1. An emulsifier composition, containing, as an emulsifier, 0.1 to 10% by weight of at least one $N^\alpha$-acylarginine alkyl ester of the formula (I):

$$R^1CONHCHCOOR^2 \quad NH \atop | \qquad \qquad \qquad \|| \atop CH_2CH_2CH_2NHC-NH_2 \qquad (I)$$

wherein:
$R^1CO$ is a mixture of straight-chain $C_{8-22}$ acyl groups;
$R^2$ is a straight-chain or branched $C_{22}$ alkyl group;
or an acid-addition salt thereof.

2. The emulsifier composition of claim 1, wherein said salt is a hydrochloride salt, sulfate salt, hydrobromide salt, hydroiodide salt, phosphate salt, acetate salt, citrate salt, p-toluenesulfonate salt, fatty acid salt, succinate salt, maleate salt, lactate salt, tartrate salt, glutamate salt, aspartate salt, or pyrrolidonecarboxylate salt.

3. The emulsifier composition of claim 1, comprising at least one of said $N^\alpha$-acylarginine alkyl ester of formula (I), an oily component and an aqueous component:
   (i) said oily component is at least one member selected from the group consisting of liquid paraffin, squalane, vaseline, microcrystalline wax, olive oil, coconut oil, tsubaki oil, Japan wax, castor oil, beeswax, spermaceti, jojoba oil, lanolin, carnauba wax, lauric acid, myristic acid, palmitic acid, stearic acid, isostearic acid, oleic acid, lanolin fatty acid, lauryl alcohol, myristyl alcohol, cetanol, stearyl alcohol, cetostearyl alcohol, oleyl alcohol, cholesterol, lanolin alcohol, octyl dodecanol, cetyl lactate, tri(capryl caprylic acid) glyceryl ester, hexyl laurate, glycerol trilaurate, isopropyl myristate, octyldodecyl myristate, cetyl myristate, myristyl myristate, glycerol trimyristate, isopropyl palmitate, butyl stearate, octyldodecyl oleate, decyl oleate, N-acyl glutamic acid higher alcohol diester, N-acyl glutamic acid polyoxyethylene octyldodecyl ether diester, and hardened oil; and
   (ii) wherein said aqueous component is at least one member selected from the group consisting of water, glycerol, propylene glycol, 1,3-butylene glycol, sorbitol, polyethylene glycol, hexylene glycol, hydrolytic protein, amino acid, sodium pyrrolidonecarboxylate, sodium lactate, sodium hyaluronate, water-soluble chitin, chitosan and derivatives thereof, ethyl alcohol, isopropanol, and salts.

4. The emulsifier composition of claim 1, comprising a thickener which is at least one member selected from the group consisting of carboxyvinyl polymer, sodium polyacrylate, sodium alginate, propylene glycol alginate, sodium carboxymethyl cellulose, methyl cellulose, ethyl cellulose, hydroxyethyl cellulose, hydroxypropyl cellulose, polyethylene glycol distearate, polyoxyethylene (120)methyl glucose dioleate, colloidal hydrated aluminum silicate (bentonite), and colloidal hydrated aluminum magnesium silicate.

5. The emulsifier composition of claim 1, further comprising polyoxyethylene alkyl ether, polyoxyethylene cholesteryl ether, polyoxyethylene sorbitan fatty acid partial ester, polyoxyethylene sorbitol fatty acid partial ester, polyoxyethylene glycerol fatty acid partial ester, polyoxyethylene phosphoric acid ester, polyoxyethylene fatty acid monoester, polyoxyethylene hardened castor oil, polyoxyethylene hardened castor oil fatty acid ester, polyglycerol fatty acid ester, cane sugar fatty acid ester, N-acyl glutamic acid polyoxyethylene alkyl ether diester, monopyroglutamic acid monofatty acid polyoxyethylene hardened castor oil, monopyroglutamic acid monofatty acid polyoxyethylene glycerol, monopyroglutamic acid monofatty acid glycerol, monofatty acid ethylene glycol, monofatty acid propylene glycol, sorbitan fatty acid partial ester, glycerol fatty acid partial ester, fatty acid alkanol amide, alkylamine oxide, N-acyl glutamic acid, N-acyl aspartic acid, and lower alkyl esters of N-long-chain acyl basic amino acids.

6. The emulsifier composition of claim 1, comprising a preservative, an ultraviolet absorbing agent, a pigment, a perfume, or an extract of a crude drug.

7. The emulsifier composition of claim 1, wherein said composition is a milky solution, a cream, ointment, a shampoo, a rinse, a hair treatment solution, a hair conditioner, or a softener.

8. The emulsifier composition of claim 1, said composition being a hair cosmetic composition or a softener composition, and comprising:

a surface active agent which is at least one member selected from the group consisting of acidic amino acids, long-chain fatty acid salts, alkyl sulfates, polyoxyethylene alkyl ether sulfates, alkyl sulfonates, α-olefin sulfonates, monoalkyl sulfosuccinates, dialkyl sulfosuccinates, polyoxyethylene alkyl sulfosuccinates, acyl monoethanolamide polyoxyethylene sulfosuccinic acid monoesters, monoalkyl phosphates, polyoxyethylene alkyl ether phosphates, acyl methyl taurine salts, acyl isethionates, N-acyl glutamic acids, N-acyl aspartic acids, N-acyl prolines, N-acyl serines, N-acyl sarcosines, N-acyl methyl β-alanines, alkyltrimethyl ammonium salts, dialkyldimethyl ammonium salts, alkyldimethylbenzyl ammonium salts, alkyl pyridinium salts, dipolyoxyethylene alkylmethyl ammonium salts, tri(polyoxyethylene)alkyl ammonium salts, 2-alkyl-1-alkyl-1-hydroxyethyl imidazolinium salts, N-cocoyl-L-arginine ethyl ester;

or an amphoteric surface active agent which is at least one member selected from the group consisting of alkyldimethyl aminoacetic acid betaine, 2-alkyl-N-carboxymethyl-Nhydroxyethyl imidazolinium betaine, higher fatty acid amide propyldimethyl aminoacetic acid betaine, N-alkyl-N,Ndimethyl-N-sulfoalkylene ammonium betaine, and N-mono long-chain acyl-N,N-dimethyl lysines.

9. The emulsifier composition of claim 1, further comprising polyvinyl alcohol, polyvinyl acetate, tragacanth gum, shellac, a methoxyethylenemaleic anhydride copolymer, polyvinyl pyrrolidone, a polyvinyl pyrrolidone-vinyl acetate copolymer, a polyvinyl pyrrolidone-dimethylaminoethyl methacrylic acid copolymer, polypeptide, cationized cellulose, lecithin, methyl polysiloxane, methylphenyl polysiloxane, a cyclic or non-cyclic silicone, polyoxypropylene butyl ether, N-lauroyl-L-lysine, zinc pyrithione, or 1-hydroxy-2-pyridone salt.

10. A $N^\alpha$-acylarginine alkyl ester of the formula (I):

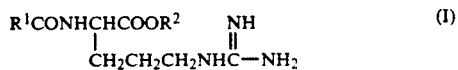

wherein:
$R^1CO$ is a mixture of straight-chain $C_{8\text{-}22}$ acyl groups;
$R^2$ is a straight-chain or branched $C_{22}$ alkyl group;
or an acid-addition salt thereof.

11. The free form of the $N^\alpha$-acylarginine alkyl ester of claim 10.

12. The $N^\alpha$-acylarginine alkyl ester of claim 10, wherein said salt is a hydrochloride salt, a sulfate salt, a hydrobromide salt, a hydroiodide salt, a phosphate salt, an acetate salt, a citrate salt, a p-toluenesulfonate salt, a fatty acid salt, a succinate salt, a maleate salt, a lactate salt, a tartrate salt, a glutamate salt, an aspartate salt, or a pyrrolidonecarboxylate salt.

* * * * *